United States Patent
Shani et al.

Patent Number: 5,728,120
Date of Patent: Mar. 17, 1998

[54] WRIST CLAMP FOR ARTERIAL COMPRESSION

[76] Inventors: Jacob Shani, 466 Mayfair Dr. S., Brooklyn, N.Y. 11234; Yonathon Hassin, 16A Kobabi Street, Ramat Denia, Jerusalem, Israel, 96757

[21] Appl. No.: 643,580

[22] Filed: May 6, 1996

[51] Int. Cl.⁶ .................................................. A61B 17/00
[52] U.S. Cl. ........................................ 606/201; 606/120
[58] Field of Search ........................ 606/201, 157, 606/120, 202, 203, 204

[56] References Cited

U.S. PATENT DOCUMENTS 3,884,240  5/1975  Gilman ................................ 606/201
4,557,262  12/1985  Snow ................................... 606/201
5,468,220  11/1995  Sucher ................................ 606/201

*Primary Examiner*—Michael Buiz
*Assistant Examiner*—Kevin Truong
*Attorney, Agent, or Firm*—Vincent J. Vasta, Jr.

[57] ABSTRACT

A device which comprises a wrist clamp which incorporates an adjustable tension screw in order to affix the clamp securely to a patient's wrist, an adjustable compression screw and pad which allows one to apply sufficient pressure to the arterial incision in order to affect adequate closure thereof while the patient's blood is coagulating, until hemostasis, after which the device may be safely removed.

4 Claims, 4 Drawing Sheets

WRIST CLAMP FOR ARTERIAL COMPRESSION

FIELD OF THE INVENTION

The present invention relates to a device for providing compression to an arterial incision in the wrist of a patient which compression is applied subsequent to an invasive procedure being performed through such an incision, which device allows the patient to be mobile and does not interfere substantially with normal activity. More particularly, the device of the present invention comprises a wrist clamp which incorporates a tension adjusting means in order to affix the clamp securely to a patient's wrist, an adjustable compression means which allows one to apply sufficient pressure to the arterial incision in order to affect adequate closure thereof while the patient's blood is coagulating, until hemostasis, after which the device may be safely removed.

BACKGROUND OF THE INVENTION

The percutaneous transfemoral approach, advocated by M. P. Judkins. Selective Coronary Arteriography, Part I: A Percutaneous Transfemoral Approach. *Radiology* 1967; 89:815-823, has been routinely used for cardiac catheterization as well as coronary angioplasty. Local vascular complications following angioplasty have been observed in 5% to 10% of patients, especially in those who need prolonged anticoagulation. This adds significantly to the morbidity involved with the procedure. Due to recent improvements and the miniaturization of angioplasty equipment, the transradial approach has been suggested as an alternative entry method for coronary angiography and angioplasty, with the potential for fewer vascular complications and improved patient comfort.

More recently, the percutaneous transradial approach for cardiac catheterization has been shown to be a safe alternative to the femoral artery approach, due to the favorable anatomical relationship of the radial artery to surrounding structures and the dual blood supply via the radial and ulnar arteries to the hand. With the miniaturization of angioplasty equipment, this approach is now being advocated as an alternative approach for coronary angioplasty, based on reduced femoral vascular complications and the ability to achieve early ambulation.

Although coronary angiography can be performed through the right or left radial arteries, the left radial approach simplifies the handling of the Judkins catheter in the ascending aorta: the course from the left subclavian into the ascending aorta is more gentle compared with angulation at the junction of the right subclavian and ascending aorta. Advantages of the left radial approach include the convenience of permitting the free use of right hand which is usually dominant, immediately after catheterization and the ability to selectively intubate left internal mammary artery in patients who have had. bypass surgery.

Nevertheless, when using the radial approach, after withdrawal of the catheter sheath, the patient is left with a substantial radial artery puncture requiring local radial compression in order to affect closure of the radial arterial wound until hemostasis.

Up until the advent of the device described in the present inventory, depending upon the amount of anti-coagulation agents employed during the procedure and other specific patient related considerations, the time during which radial compression was required could vary significantly and generally involved the combination of manual pressure being applied by one of the medical staff in conjunction with the subsequent immobilization of the patient's wrist/hand for an extended period of time during which the patient would be essentially totally immobilized.

The applicant is not aware of the existence of any prior art device which is available to the art which incorporates all of the essential features of the wrist clamp of the present invention.

It is, therefore, an object of the present invention to provide for a device for compression of an arterial incision which has been made in the wrist of a patient which compression is applied subsequent to an invasive procedure being performed through such incision.

It is a further object of the present invention to provide for a device for compression of an arterial incision in the wrist of a patient which compression is applied subsequent to an invasive procedure being performed through such an incision and which device allows the patient to be mobile and does not substantially interfere with normal activities.

It is yet another object of the present invention to provide for a device which comprises a wrist clamp which incorporates an adjustable tension means in order to affix the clamp securely to a patient's wrist and an adjustable compression means which allows one to apply sufficient pressure to the arterial incision in order to affect. adequate closure of the incision until hemostasis.

Lastly, it is an object of the present invention to. provide for a device which comprises a wrist clamp which incorporates an adjustable tension means in order to affix the clamp securely to a patient's wrist and an adjustable compression means which allows one to apply sufficient pressure to the arterial incision in order to affect adequate closure of the incision until hemostasis, wherein the location and tension applied by the compression means is adjustable in three dimensions and the device is also adjustable to accommodate patient wrists of various sizes.

These and other objects of the invention will become apparent from the following discussion of the invention.

SUMMARY OF THE INVENTION

The present invention provides for a device which comprises a wrist clamp which incorporates an adjustable tension means in order to affix the clamp securely to a patient's wrist, an adjustable compression means which allows one to apply sufficient pressure to the arterial incision in order to affect adequate closure thereof while the patient's blood is coagulating, until hemostasis, after which the device may be safely removed.

The present invention also provides for a device which comprises a wrist clamp wherein the location and tension applied by the adjustable compression means to the arterial incision is adjustable in three dimensions and wherein the device is also adjustable to accommodate patient wrists of various sizes.

The construction and obvious advantages of the system provided for by the present invention will be more clearly understood from the following description of the various specific embodiments when read in conjunction with the accompanying drawings.

DETAILED DESCRIPTION OF THE INVENTION

The present invention is directed to a device which comprises a wrist clamp which incorporates an adjustable tension means in order to affix the clamp securely to a patient's wrist, an adjustable compression means which allows one to apply sufficient pressure to the arterial incision in order to affect adequate closure thereof while the patient's blood is coagulating, until hemostasis, after which the device may be safely removed.

Figure 1:
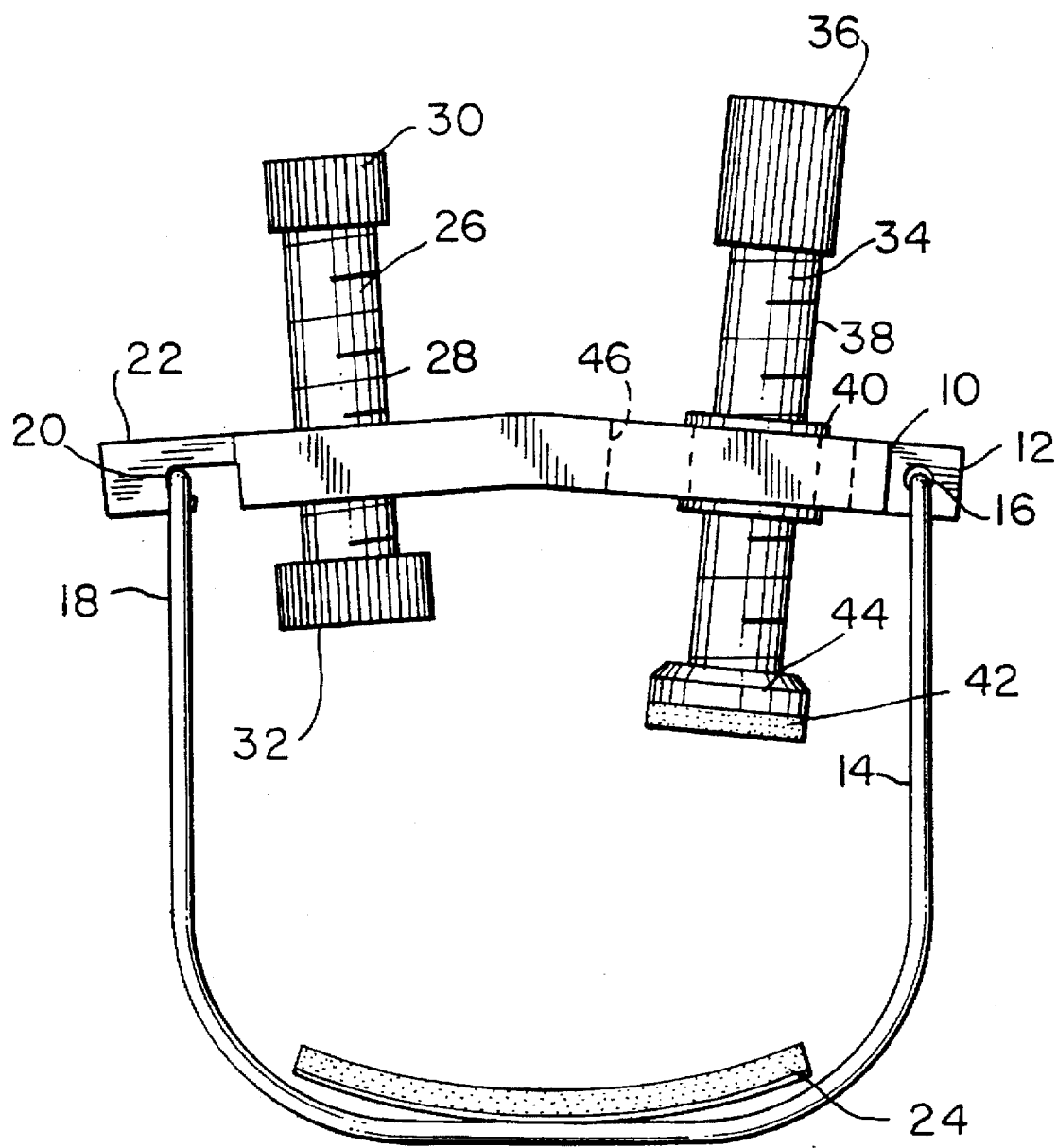
FIG. 1 is a schematic representation of a front elevation view of the device of the present invention showing the relative location of the various elements.

With reference to FIG. 1, which depicts the front view of a preferred embodiment of the wrist clamp of the present invention, it can be seen that the device of the present invention comprises a generally flat header assembly 10 which is attached at one end 12 to a generally U-shaped wrist retainer 14 which rotates about a pivot means 16 located at one end of the header assembly while the other end 18 of the U-shaped wrist retainer engages a retaining means 20 located at the opposite end 22 of the header assembly. A portion of the U-shaped wrist retainer is defined by a wrist pad 24 to comfortably cradle the patient's wrist. The header assembly 10 is provided with an adjustable tension means 26, comprising a threaded short portion 28, having a knurled fixed turning end portion 30 and a compression pad portion 32 at the opposite end, which tension means may be manually adjusted to provide sufficient tension on the patient's wrist in order to firmly secure the wrist clamp thereto. The header assembly is also provided with an adjustable compression means 34 which consists of a knurled fixed turning end portion 36, a threaded portion 38, a slide means 40 through which the threaded portion of the compression means is attached to the header assembly, and a compression pad means 42 which is attached to the end of the threaded portion via a rotating gimbal assembly 44. The slide means 40 is engaged in a slot 46 which is provided in the header assembly in order to allow for the adjustment of the compression means in a lateral direction, thereby allowing for proper placement of the compression means over the arterial puncture.

Figure 2:
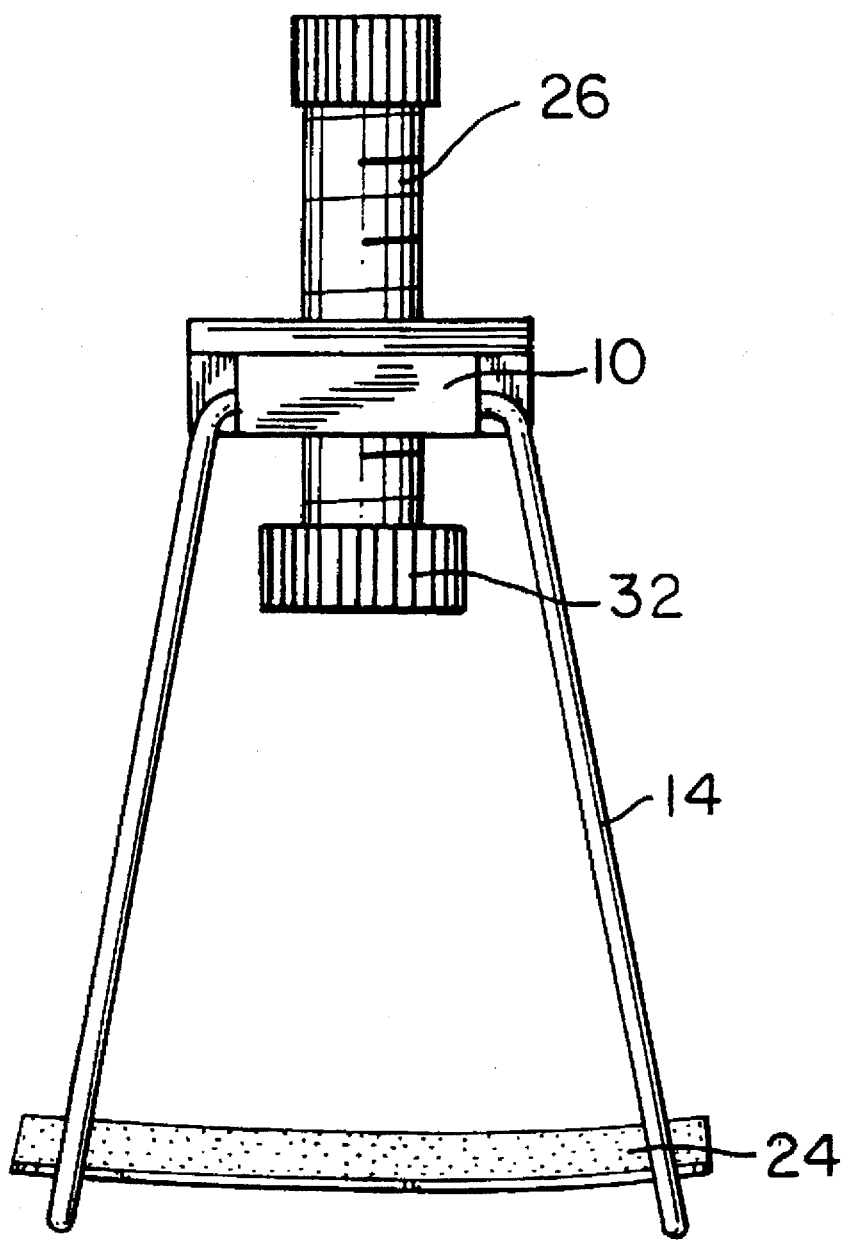
FIG. 2 is a left side elevation view of the device of the present invention.

With reference to FIG. 2 which depicts the less left side elevation view of the preferred embodiment depicted in FIG. 1, the relative geometry of the header assembly 10, the wrist retainer 14, the wrist pad 24, the adjustable tension means 26, and the compression pad 32, are shown.

Figure 3:
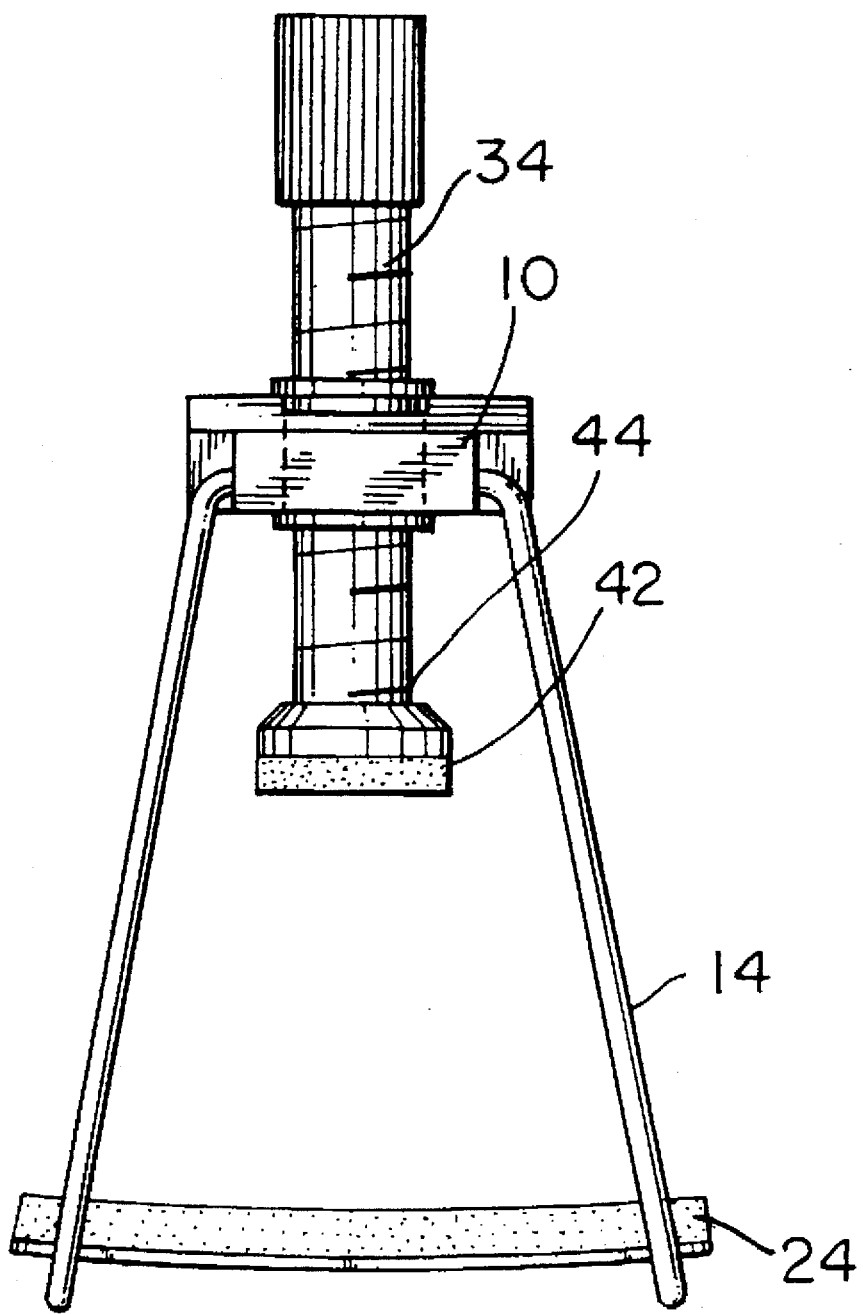
FIG. 3 is a right side elevation view of the device of the present invention.

With reference to FIG. 3 which depicts the right side elevation view of the preferred embodiment depicted in FIG. 1, the relative geometry of the flat header assembly 10, the wrist retainer 14, the wrist pad 24, the adjustable compression means 34, with its attached compression pad means 42, and the rotating gimbal assembly 44, can be seen.

Figure 4:
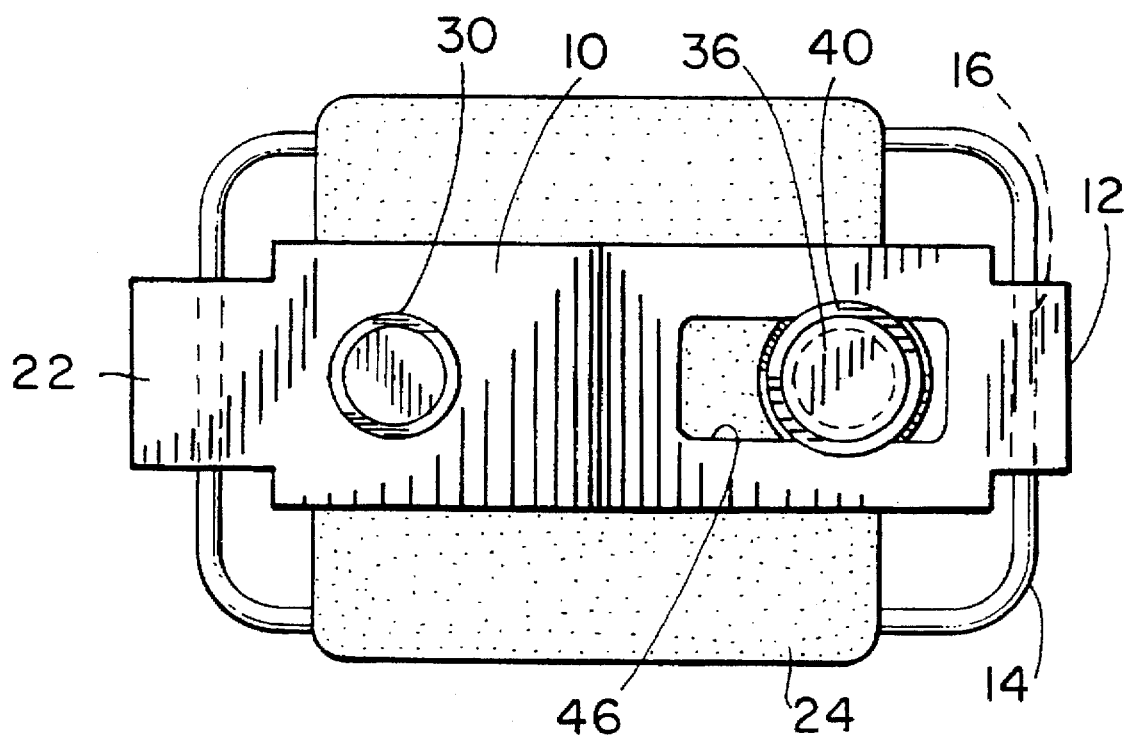
FIG. 4 is a top plan view of the device of the present invention.

With reference to FIG. 4, which depicts a top plan view of a preferred embodiment of the wrist clamp depicted in FIG. 1, it can be seen that the header assembly 10 is notched at one end 12 to accommodate the pivot means 16 about which the U-shaped wrist retainer 14 pivots. The knurled fixed end of the adjustable tension means 30 is shown with relation to the knurled fixed end 36 of the adjustable compression means. The relationship of the slide means 40 and the slot 46 in which the slide means is engagingly disposed is also shown.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here.

I claim:

1. A wrist clamp for arterial compression which fully encompasses the user's wrist which comprises a header assembly having an adjustable tension means wherein the mount of tension force applied is adjustable by the person applying the wrist clamp while on the patient's wrist in order to affix the clamp securely to a patient's wrist, an adjustable compression means which allows one to apply sufficient pressure to the arterial incision in order to affect adequate closure thereof while the patient's blood is coagulating, until hemostasis.

2. A wrist clamp according to claim 1, which comprises a generally flat header assembly which is attached at one end to a generally U-shaped wrist retainer, which retainer rotates about a pivot means located at one end of the header assembly, the other end of which U-shaped wrist retainer engages a retaining means located at the opposite end of the header assembly, wherein a portion of the U-shaped wrist retainer is defined by a wrist pad and wherein said header assembly is provided with the adjustable tension means and the adjustable compression means in order to apply sufficient pressure to the arterial incision in order to effect adequate closure thereof while the patient's blood is coagulating.

3. A wrist clamp according to claim 1, wherein the adjustable tension means provided in the header assembly comprises a short threaded portion having a knurled fixed turning end portion at one end of the threaded portion and a compression pad portion at the opposite end of the threaded portion.

4. A wrist clamp according to claim 1, wherein the adjustable compression means comprises a knurled fixed turning end portion, a threaded portion, a slide means through which the threaded portion is attached to the header assembly and a compression pad means which is attached to the end of the threaded portion via a rotating gimbal assembly, wherein the slide means is engaged in a slot which is provided in the header assembly in order to allow for the adjustment of said compression means in the lateral direction, thereby allowing for proper placement of the compression means over the arterial puncture.

* * * * *